United States Patent [19]
Herrmann et al.

[11] Patent Number: 5,804,739
[45] Date of Patent: Sep. 8, 1998

[54] METHOD AND CIRCUIT ARRANGEMENT FOR THE MEASUREMENT OF FLOW SPEED BY MEANS OF ACOUSTICAL TRANSIT TIME DIFFERENCES

[75] Inventors: Volker Herrmann; Horst Koepernik, both of Dresden, Germany

[73] Assignee: Erwin Sick GmbH Optik-Elektronik, Waldkirch/Breisgau, Germany

[21] Appl. No.: 662,721

[22] Filed: Jun. 10, 1996

[30] Foreign Application Priority Data

Jun. 22, 1995 [DE] Germany .................. 195 22 697.6

[51] Int. Cl.⁶ .................................................. G01F 1/20
[52] U.S. Cl. ................................. 73/861.18; 73/861.27
[58] Field of Search ....................... 73/579, 861.18, 73/861.27, 861.28, 597, 861.31

[56] References Cited

U.S. PATENT DOCUMENTS

| | | | |
|---|---|---|---|
| 3,914,998 | 10/1975 | McShane | 73/861.28 |
| 4,052,896 | 10/1977 | Lee et al. | 73/861.28 |
| 4,384,491 | 5/1983 | Brown et al. | 73/861.28 |
| 4,417,481 | 11/1983 | Krause | 73/861.28 |
| 4,480,485 | 11/1984 | Bradshaw et al. | 73/861.28 |
| 4,603,589 | 8/1986 | Machida | 73/861.28 |
| 5,035,147 | 7/1991 | Woodward | 73/861.28 |
| 5,052,230 | 10/1991 | Lang et al. | 72/861.28 |
| 5,123,286 | 6/1992 | Baumgärtner | 73/861.27 |
| 5,178,018 | 1/1993 | Gill | 73/861.28 |

FOREIGN PATENT DOCUMENTS

| | | | |
|---|---|---|---|
| 0 051 293 | 5/1982 | European Pat. Off. | A61B 5/08 |
| 0 212 060 | 3/1987 | European Pat. Off. | G01H 3/00 |
| 0 407 676 A1 | 1/1991 | European Pat. Off. | G01F 1/66 |
| 0 324 731 B1 | 3/1993 | European Pat. Off. | G01S 7/52 |
| 29 32 005 | 2/1980 | Germany | G01F 23/28 |
| 29 23 963 | 11/1980 | Germany | G01R 29/02 |
| 30 16 968 C2 | 11/1982 | Germany | G01P 5/00 |
| 3436639 A1 | 4/1986 | Germany | G01B 7/03 |
| 39 23 349 C2 | 5/1991 | Germany | G04F 10/00 |
| 43 22 849 C1 | 12/1994 | Germany | G01S 15/88 |
| 2 176 894 | 1/1987 | United Kingdom | G01F 1/66 |
| WO 93/00569 | 1/1993 | WIPO | G01F 1/66 |

OTHER PUBLICATIONS

Patent Abstracts of Japan, vol. 007, No. 231 (P-229), Oct. 13, 1983 & JP-A-58 120119 (Kansai Denriyoku KK: Others: 01), Jul. 16, 1983, Abstract.

*Primary Examiner*—Hezron E. Williams
*Assistant Examiner*—Richard A. Moller
*Attorney, Agent, or Firm*—Townsend and Townsend and Crew LLP

[57] ABSTRACT

A method of determining the time point ($t_0$) of the start of a high frequency oscillation packet triggered as a result of a corresponding external excitation which is extremely tolerant relative to systematic disturbances from various sources consists of determining the times at at least two points of the envelope curve of the oscillation packet with respect to an arbitrary zero time point. Of these two points one is a characteristic point of the envelope curve and the other has an amplitude equal to a predetermined fraction of the amplitude at the characteristic envelope curve point.

16 Claims, 5 Drawing Sheets

Fig. 3

METHOD AND CIRCUIT ARRANGEMENT FOR THE MEASUREMENT OF FLOW SPEED BY MEANS OF ACOUSTICAL TRANSIT TIME DIFFERENCES

FIELD OF THE INVENTION

The invention relates to a method for determining the time point of the start of a high frequency oscillation packet, in particular of an ultrasonic oscillation packet, triggered as a result of a corresponding external excitation. The invention also relates to a circuit arrangement for carrying out such a method. Furthermore, the invention relates to a method of recognizing changes of the oscillation characteristics of high frequency oscillation transmitters and receivers, in particular of ultrasonic converters, the quality and/or resonance frequency of which can change in the course of time.

DESCRIPTION OF PRIOR ART

It is known to determine the flow speeds of gases from the transit time difference of ultrasonic pulses transmitted into the gas in opposite directions (see, for example, German patent 43 22 849 C1), with an angle which differs substantially from 90° and which should, for example, lie in the order of magnitude of, for example, 45°, being present between the direction of propagation of the ultrasonic pulses and the flow direction of the gas. Thus a very precise determination of the transit time differences of the ultrasonic pulses is required. A measurement error of only 10 µs already leads to a deviation of approximately 0.45 m/s in the calculation of the speed, with a measurement path of 3 m and with a 45° inclination between the propagation direction of the ultrasonic pulses and the gas flow direction and also at 200° C. gas temperature. Narrow band ultrasonic converters, which are preferred because of their robustness and their high transmitter power, require a signal length of several milliseconds, i.e. approximately one thousand times the desired time resolution.

Random errors arise during the transit time measurement through turbulence and temperature gradients in the gas and through amplitude fluctuations, through transit time fluctuations, and through pulse shape fluctuations of the measurement signals which are generated thereby. These errors can be largely reduced by average value formation or by correlation methods. In addition, however, systematic errors also occur which cannot be compensated for by the known methods. Sources of systematic measurement errors can be found both in the measurement path and also in the converters.

Thus, reflections occur in the channel which contains the measurement path which lead to a superposition of the ultrasonic pulse and its reflected components. Depending on the phase position, the original signal is thereby amplified or attenuated and thus the shape of the envelope curve is changed. Since such reflections are dependent on the channel geometry, they can have different effects on the two sound directions and can cause zero point errors via systematic shape differences.

The reflected signal components which influence the pulse shape due to interference are delayed relative to the direct signal because of their longer transit paths. Accordingly, the start of the signal is still undisturbed and the interferences first become effective in the further course of the signal. In accordance with the invention, the signal components which appear at the beginning should thus be used to obtain the time information and in this way the influence of disturbing interferences should be largely precluded.

The ultrasonic converters do not have precisely the same characteristics, even in the new state, as a consequence of manufacturing tolerances and inhomogeneities of the material. Changes occur due to temperature, aging and corrosion effects and also because of contamination by dusty media which have an effect on the quality factor and on the resonant frequency. The transducer quality factor thereby influences the steepness of the build-up and decay of the oscillation, whereas differences between the excitation frequency and the resonant frequency produce more complicated changes in shape. Because of the inclination of the measurement path relative to the flow direction which differs from 90°, the upstream converter, onto which the gas flow is directly incident, is exposed to the above-named influences to a greater degree than the other converter. The different converter characteristics bring about correspondingly differing shapes of the received signals, which leads to systematic measurement errors with most of the time recording methods.

A method and an apparatus for the transit time measurement of ultrasonic signals has become known (U.S. Pat. No. 4,630,482) in which the digitized scanned values of the received signals are added up in associated storage cells until a predetermined value is achieved in one of the storage cells. The address of the cell is evaluated as the transit time. In this arrangement any systematic change in shape of the received signals, for which the time spacing from the start up to the maximum of the signal changes, falsifies the measured times.

Furthermore, it is known (EP 0 407 676 B1) not to use the maximum of the signal as the time reference but rather to use the attainment of a threshold value derived from the maximum value. In this way the time spacing between the start of the signal and the time recording is reduced as well as, approximately in proportion thereto, the influence of fluctuating rise times. However, a substantial compensation of shape-dependent measurement errors cannot be achieved in this way.

OBJECTS OF THE INVENTION

It is thus the object of the present invention to ensure an ideal time recording which is largely free of systematic errors even when the reflection conditions in the measurement channel and the characteristics of the ultrasonic converter change. In particular the accuracy and resistance to interference should be increased with flow speed measurements made in accordance with the acoustic transit time difference method.

BRIEF DESCRIPTION OF THE INVENTION

In accordance with the present invention, the time origin of a high frequency received signal, in particular of an ultrasonic received signal, is so determined from its envelope curve that changes of shape and rise time of the signal have the smallest possible influence on the accuracy of the transit time difference that is determined.

The true zero time point of an individual oscillatory packet is of subordinate importance. In contrast, of importance is the reproducibility with respect to the individual transit times which is the determining factor for the high accuracy of the transit time difference measurement. In this way the resistance to interference of the speed measurement by means of acoustic transit time differences is also simultaneously increased. A particular feature of the method of the invention and of the circuit arrangement of the invention is the high error tolerance relative to systematic changes at the transducers. Thus good measurement accuracy, reproducibility and reliability are possible with reduced complexity. Thus, by way of example, the cost intensive additional devices described in the above-mentioned DE 43 22 849 C1 at the converters and the use of the costly correlation method which is complicated computerwise are avoided.

The concept underlying the invention is thus to be seen in the fact that the time recording not only takes place at one but rather at two threshold values of the rise of the envelope curve (two, threshold time recording). By the choice of suitable relationships of the thresholds at which time recordings are made or of the amplitudes in relation to the pulse maximum, it is possible to almost make the influence of quality changes of the converters on the transit time which is found disappear.

The use of the point of inflection as a characteristic envelope curve point has the advantage that the higher and timewise later threshold is still located relatively close to the start of the signal. Here interferences which are produced by vagabond scattering signals are not present, or are only present to a small degree.

In accordance with the present invention, the influence of frequency dependent pulse shape changes on the two threshold time recording are reduced in that it is preferably not the amplitude maximum which is taken as the reference value for the calculating of the threshold level but rather the maximum steepness of the envelope curve which arises earlier timewise and is thus less disturbed. This reference value can also be used to minimize the influence of the quality factor with the same threshold ratio. At the same time the choice of this reference value reduces the above-mentioned influence of reflection-dependent changes in shape.

The height ratio or amplitude ratio of the time recording thresholds has a substantial influence on how well changes in pulse shape can be compensated for with the method. In accordance with the invention the height ratio is so selected that essentially the same time intervals exist between the zero time point and the first and second time recording points in order to obtain an ideal compensation effect.

The two-threshold time recording process does not, however, have an unlimited scope of application. It relates to changes of the transducer characteristics which arise in normal operation and not to serious disturbances. If these disturbances do not cause a total failure of one or both transducers, then measurement errors which they cause could remain undiscovered for a longer period of time.

For this reason the above-described time recording method of the invention is supplemented by a test method which recognizes deviations of the transducer characteristics from the normal behavior and signalizes them in a suitable manner. Moreover, with the aid of this test method a determination can be made, since it only concerns the transducer, whether the causes of the fault are to be sought in the transducer or also in the transmission path if no adequate sound pressure for measurement should be present. The method relates to the dependence of the current plot measured during transmission on the state of the relevant converter. In this respect changes of the resonant frequency and other further characteristics have a particularly pronounced effect on the curve shape of the excitation current.

In accordance with the test method of the present invention, the sensed values of the excitation currents for intact converters which are in resonance are stored. In test routines, which are inserted into the normal measurement operation at certain time intervals, a comparison takes place between the actual excitation current plot and the stored excitation current plot. If the so derived differences exceed a predetermined amount, then this is recognized by the measurement device. The reaction of the apparatus can then take place separately in accordance with the detected fault mechanism. If the time differences simply exceed the predetermined tolerances, then a warning signal is given, and the measurement can, however, be continued. The warning signal shows that the accuracy is restricted and that a repair should be made. If the amplitude and phase criteria also exceed the preset amount of the tolerance, then a fault message is transmitted and the measurement is broken off.

In one embodiment, digitized, scanned values of the transducer current flowing with a defined excitation are evaluated with digitized, scanned values of the excitation current of a converter in a comparison state that are stored in a memory of a control/evaluation unit. Resulting difference values are evaluated for fault recognition.

An important basic concept of the present invention is thus that the reliability of a measurement apparatus/measurement method against disturbance is increased. The two threshold methods operate reliably only within the defined working range of the ultrasonic transducers. These transducers can also have other errors than these changes which do not lead to total failure.

DESCRIPTION OF PREFERRED EMBODIMENTS

Figure 1:
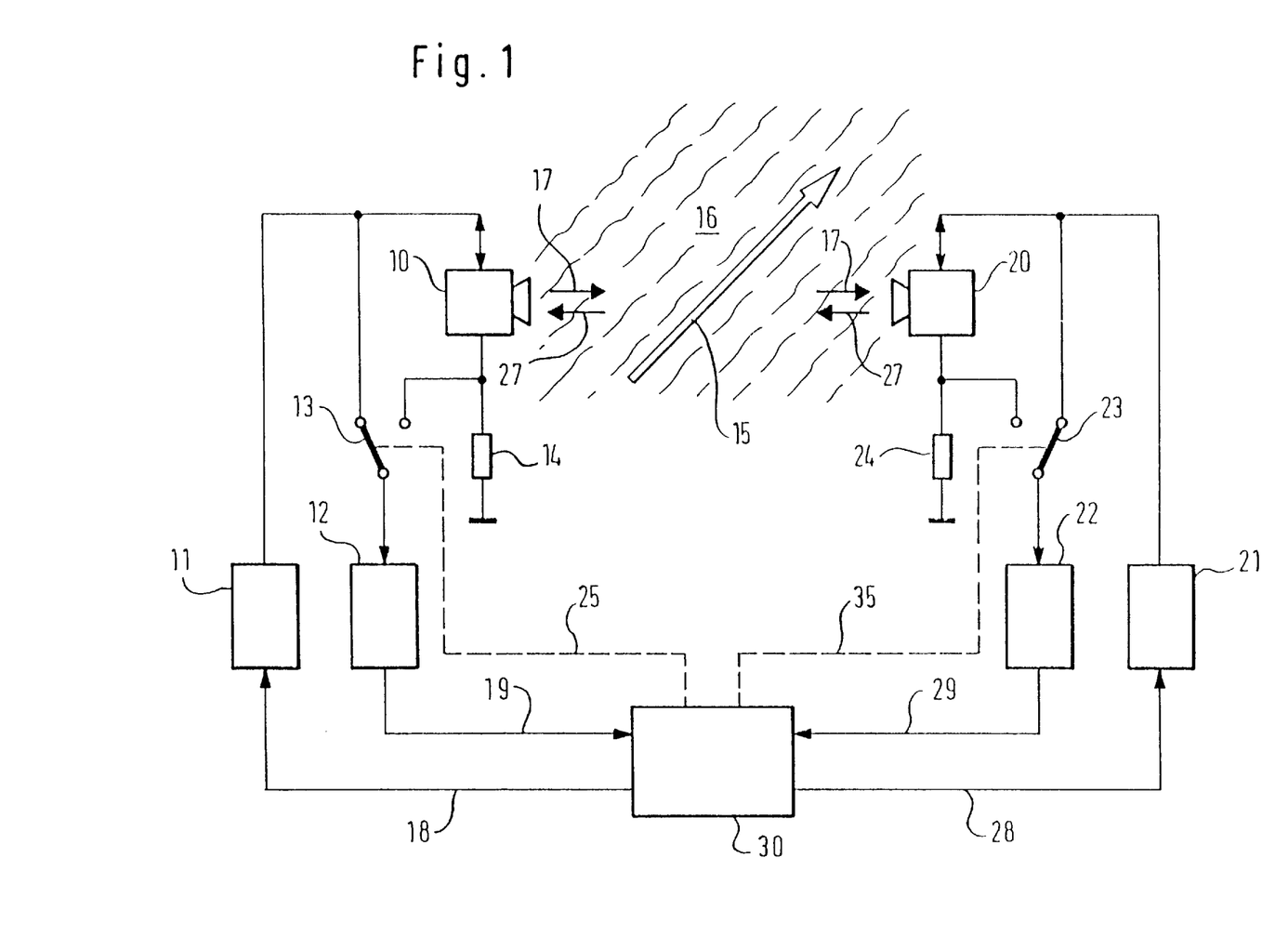
FIG. 1 is a block circuit type representation of a circuit arrangement in accordance with the present invention with two ultrasonic converters arranged in a flowing medium.

In accordance with FIG. 1, two ultrasonic converters 10, 20 are provided which are arranged on opposite sides of a preferably gaseous medium 16 flowing in the direction of the arrow 15, and which are connected to earth via very small resistances 14 and 24 respectively, with the ultrasonic converters 10, 20 standing in connection with transmitter stages 11 and 21 respectively to excite oscillations thereof. In this manner the transducers 10, 20 can alternately send ultrasonic pulse packets into the medium 16 in the direction of the arrows 17, 27 at an angle of approximately 45° to the flow direction 15 of the medium 16.

The receiver stages 12 and 22 respectively can be connected via respective change-over switches 13 and 23 either to the pole of the ultrasonic converter 10, 20 connected to the transmission stage 11 and 21 respectively or to the connection point between the converters 10, 20 and the resistors 14 and 24 respectively.

The transmitter stages 11, 21 and the receiver stages 12, 22 are respectively connected to a control/evaluation unit 30 which controls the transmitter stages 11, 21 via lines 18, 28, and optionally also feeds them, and which processes the received signals received from the receiver stages 12, 22 via the lines 19, 29. The control/evaluation unit 30 is furthermore connected via control lines 25, 35 to the change-over switches 13 and 23 respectively in order to be able to bring these into the one or other switch position. The position of the change-over switches 13 and 23 respectively shown in FIG. 1 corresponds to the normal measurement operation during which, in a first cycle of the ultrasonic transducer excited by the transmitter 11 brought about by the control/evaluation unit 30, ultrasound is transmitted once or several times after one another in the form of a high frequency pulse packet in the direction of the arrow 17. The ultrasound pulses are also received after passing along the measurement path in the medium 16 by the ultrasonic transducer 20 which has been switched to reception by the control/evaluation unit 30 and are converted into electrical signals which are supplied via the switch 23 and the receiver 22 to the control/evaluation unit 30 in which the transit time required for this direction from the ultrasonic pulses is determined as the time difference between the transmission and reception of a pulse packet, or of each pulse packet.

In a second cycle the control/evaluation unit 30 switches the ultrasonic converter 10 to reception and the ultrasonic converter 20 to transmission, whereupon the ultrasonic converter 20 transmits pulses through the medium 16 in the direction of the arrow 27 to the ultrasonic converter 10 which is now working as a receiver and which converts the received signals into electrical signals and passes them on via the receiver 12 to the control/evaluation unit 30. The control/evaluation unit 30 calculates the flow speed of the medium 16 in the direction of flow 15 from the difference of the transit times of the pulse packets calculated during this measurement and previously for the opposite direction in a well-known manner. During this calculation the angle between the directions 17, 27 of the ultrasonic pulse packets and the flow direction 15 of the medium 16, which differs significantly from 90°, is particularly taken into account.

Figure 2:
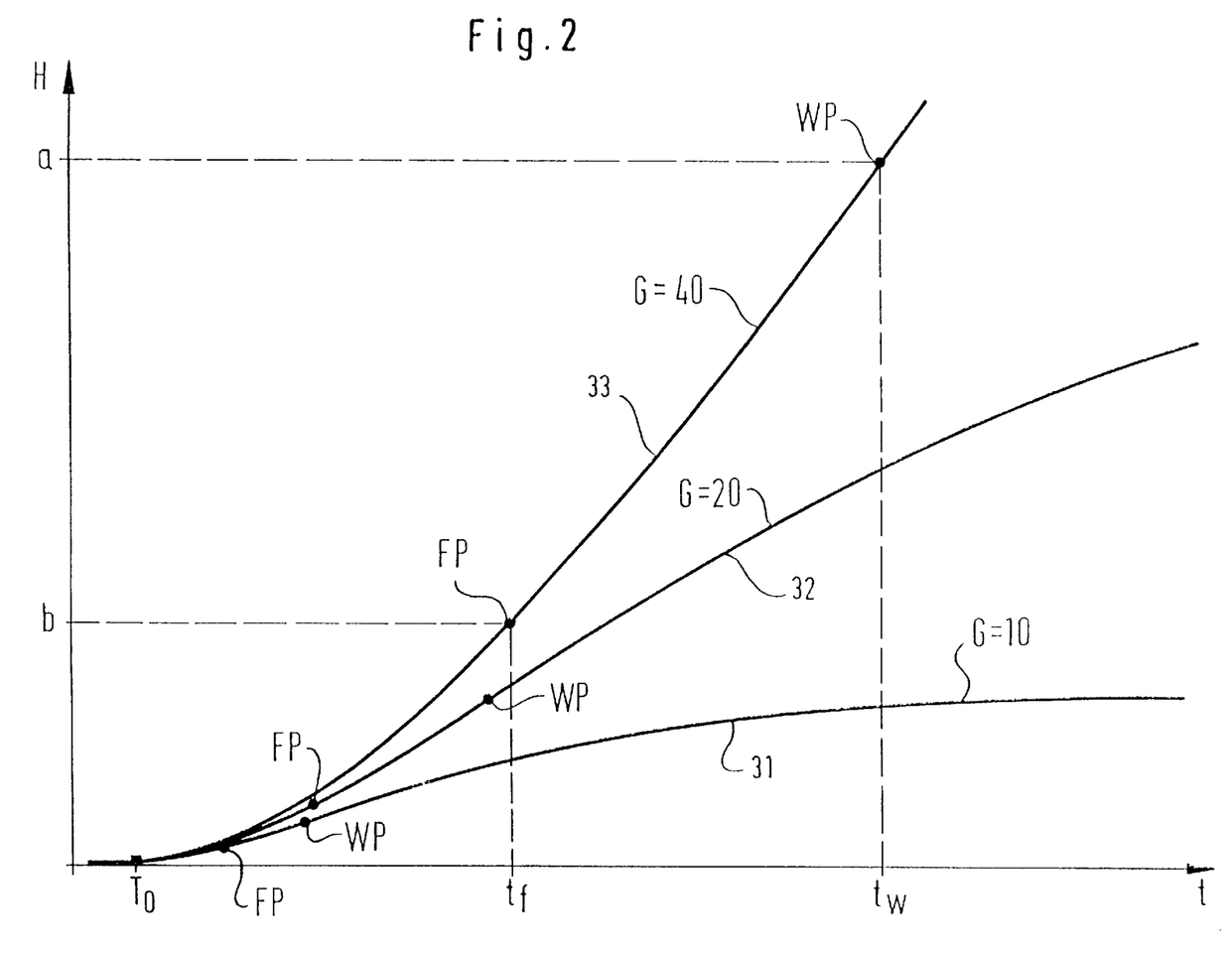
FIG. 2 shows three envelope curves which arise with very different quality factors of a pulse packet signal received by the respective receiver/ultrasonic converter.
Figure 3:
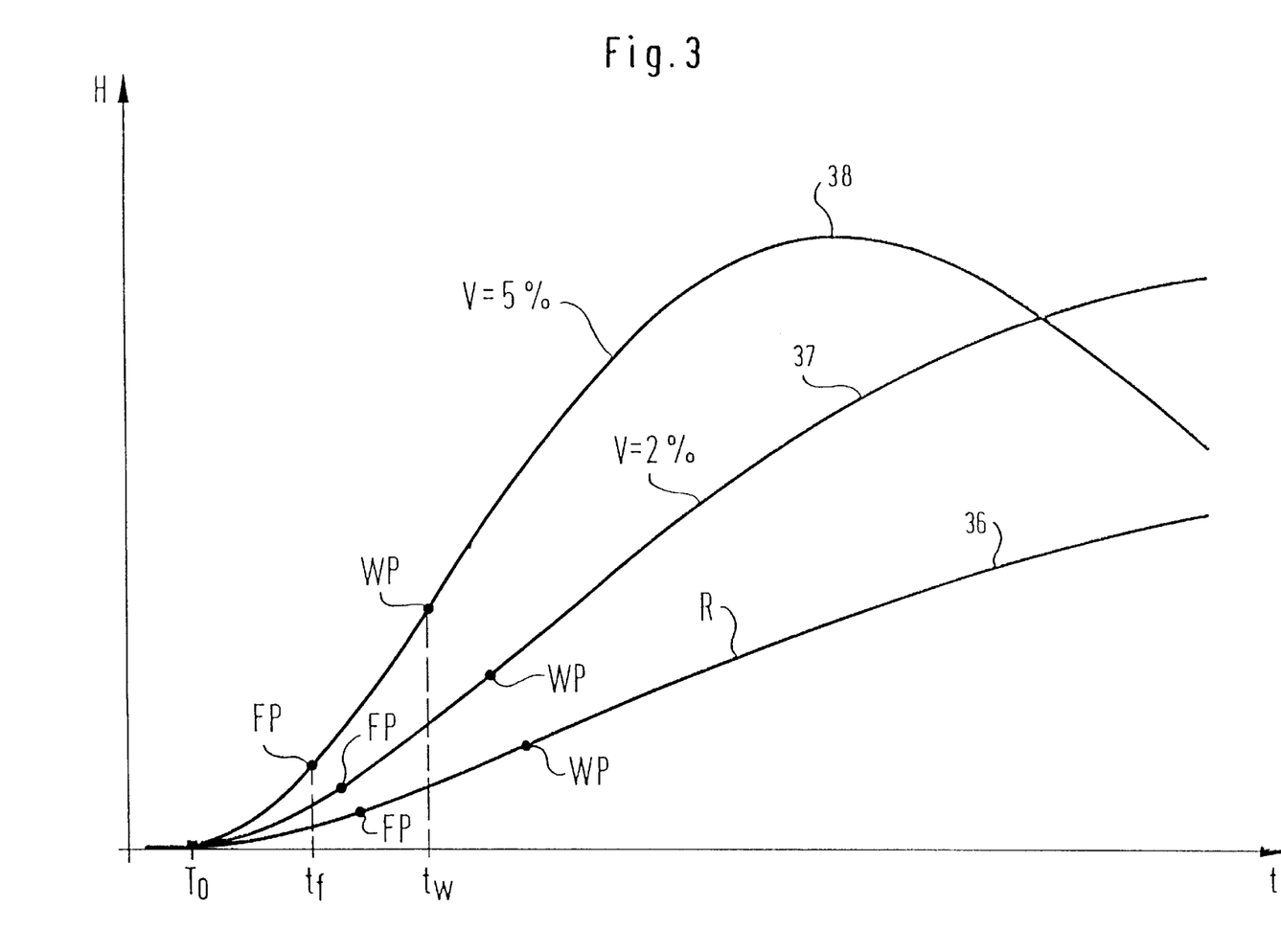
FIG. 3 shows a similar envelope curve illustration to that shown in FIG. 2 but with three different states of tuning of the receiver converter.

The diagrams of FIGS. 2 and 3 demonstrate the effect of the two-threshold time recording in accordance with the invention. The constant sinusoidal excitation of the ultrasonic transducer 10 or 20 respectively starts delayed by one period relative to the left-hand edge of the two Figures. The FIGS. 2 and 3 in each case show the envelope curve determined by the squaring method of the rising AC voltage which respectively appears at the oppositely disposed converter 20 or 10. The amplitude A of the alternating voltage is shown on the ordinate and the time t is recorded along the abscissae.

The squaring method or quadrature method is a demodulation method known in communication technology for sinusoidal signals. The envelope curve points thereby result as squared average values of the sensed value A of the original signal obtained at spacings of a quarter period. The symmetrical form of the method with three sensed values A in accordance with the following formula $$H(t)=A(t)^2+A(t-T/4)^2+A(t)^2+A(t+T/4)^2 \quad (1)$$

where

H(t)=envelope curve value at the time t
A(t)=sensed value of the time t
T=1/f=duration of a period
f=signal frequency of the high frequency pulse packet.

results in a particularly good approach to the ideal envelope curve.

The upper time recording threshold now passes, in accordance with the invention, through the inflection point WP (point of greatest steepness) of the envelope curve. The time zero point $t_0$ is calculated in accordance with the invention in accordance with the following formula:

$$t_0=(k^*t_f-t_w)/(k-1) \quad (2),$$

wherein:

$t_w$ signifies the time measured from an arbitrarily selected zero time point until the point of inflection is reached, $t_f$ signifies the time measured from the same arbitrarily selected time point at which the predetermined fraction of the envelope curve value at the point of inflection WP is measured, and k signifies the reciprocal of the predetermined fraction of the envelope curve value at the point of inflection WP, i.e. the reciprocal ratio of the envelope curve value a at the point of inflection WP relative to the envelope curve value b which corresponds to the predetermined fraction b of the envelope curve value at the point of inflection WP.

If k=2 then this formula simplifies as follows:

$$t_0=2^*t_f-t_w \quad (3).$$

A constant k=2.94 has proven to be ideal.

In FIG. 2 three envelope curves 31, 32, 33 are drawn in for different qualities G=10, G=20, and G=40 respectively of the receiving ultrasonic converter. On each envelope curve the point of inflection WP and the so-called fraction point FP are reproduced at which the envelope curve value b has a predetermined fraction, for example 0.34 of the value of the envelope curve a at the location of the point of inflection WP. The reciprocal of this value, i.e. the quotient b/a, is the same as the constant K.

In FIG. 2 the actual zero point of the high frequency oscillation packet is designated by $T_0$. The zero time point $T_0$ calculated in accordance with the invention does admittedly not precisely coincide with the actual zero time point $T_0$. However, the deviations from this in practice are negligible, although a quality factor change of 1:4 was assumed which in practice will hardly be encountered. The reason for the negligibility is that the reproducibility for individual measurements is decisive in order to achieve a high accuracy in the transit time difference measurement.

FIG. 3 shows the envelope curves of the high frequency oscillation packets received by the ultrasonic converter 10 or 20 respectively at resonance R, with detuning V of 2% or with detuning V of 5%. One recognizes that even with these extreme differences of the envelope curves, the zero points $t_0$ of the different envelope curves 36, 37, 38 which are calculated lie close together and also lie close to the actual zero time point $T_0$.

Detuning of the oscillating circuits, which in practice corresponds to temperature and aging dependent transducer resonance, produces a complicated shape of the envelope curve which is characterized by vacillations between excitation frequency and natural frequency. These changes in shape, however, remain relatively small up to the point of inflection of the envelope curve so that the selection of this point as a characteristic envelope curve point is particularly advantageous. In the embodiment of FIG. 3 the excitation has also been varied in addition to the detuning in order to be able to better distinguish the curves. This has no influence on the calculated zero point because of the pure scale function of the curves. Despite a very pronounced change in shape of the envelope curve at 5% detuning, the calculated zero points only have relatively small deviations from one another and from the true zero time point for the same size of the predetermined fraction which, as shown in FIG. 2, has been assumed to have the ideal value of 0.34.

From time to time a testing of the transducers takes place in order to timely determine substantial changes in their characteristics so that no measurement inaccuracies can be produced hereby.

For the purpose of testing, resistors 14 and 24 respectively are provided in FIG. 1. During testing the switches 13 and 23 respectively are so switched over that the connection points between the ultrasonic converters 10 and 20 with the resistor 14 and 24 respectively are connected to the associated receivers 12 and 22 respectively.

In a first test cycle, the transmitter stage 11 applies a defined pulse signal to the transducer 10. The transducer current thereby generates a voltage drop at the resistor 14 which is transmitted via the switch 13 to the receiver 12 and, after corresponding amplification, to the control/evaluation unit 30. Here the current signal of the ultrasonic converter 10 is compared with a desired signal stored on taking the apparatus into use. If the difference which is thereby found exceeds a predetermined threshold then this state is signalized in the above-described manner. In any event, the control/evaluation unit 30 prevents the apparatus from continuing to operate, in the case of such a deviation, without giving a corresponding warning or fault indication.

In a second test cycle, the analogous procedures are effected at the ultrasonic converter 20 with the participation of the transmitter stage 21, of the receiver 22, and of the resistor 24. A switching off through the control/evaluation unit 30 also takes place here, providing the current signal of the ultrasonic converter 22, which is generated when the resistor 24 becomes effective, is compared with a desired signal stored in the control/evaluation unit 30 on taking the apparatus into operation, and further providing a difference is detected which exceeds a preset threshold.

If, during the two test cycles, the control/evaluation unit 30 finds that the differences between the two actual test transducer currents and the desired signals stored in the control/evaluation unit 30 remain within the preset error limits, then the switches 13, 23 are switched again into the position evident from FIG. 1 and the normal measurement operation is continued.

Figure 4:
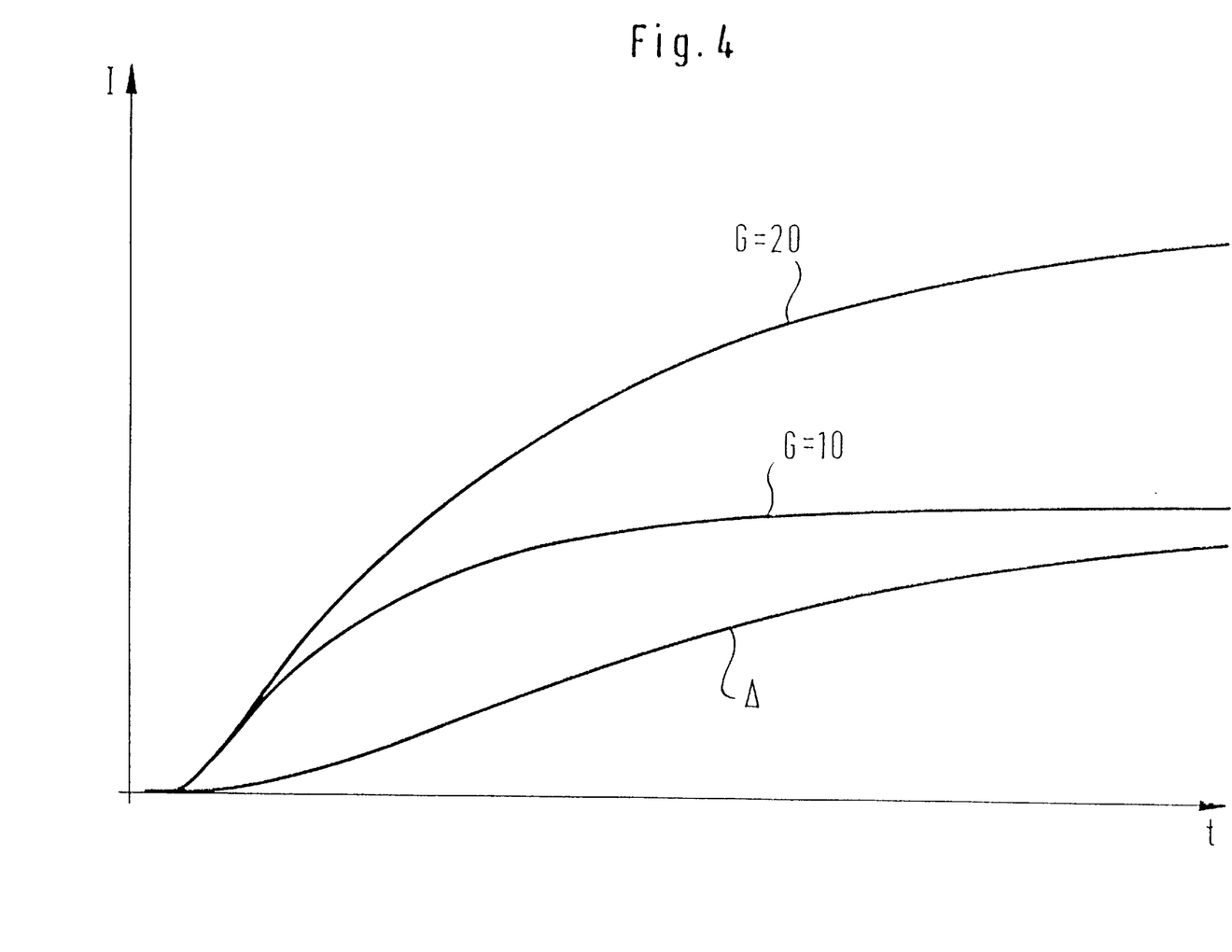
FIG. 4 shows the time dependence of the demodulated current in the transmitter converter with two different transducer quality factors and the error difference in dependence on the time at resonance and at constant excitation.
Figure 5:
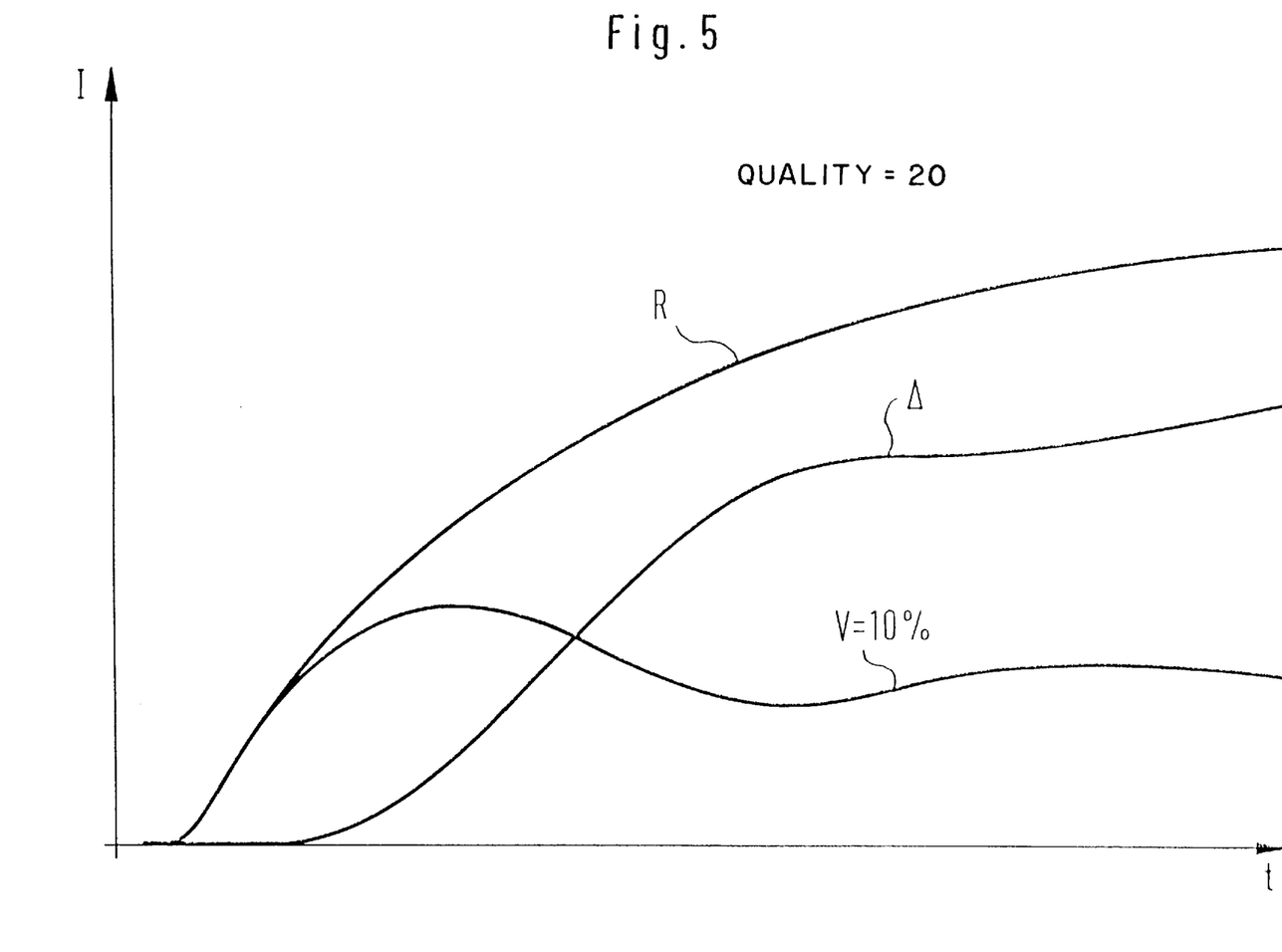
FIG. 5 is a similar diagram to FIG. 4 with the time dependence of the demodulated current in the transmitter converter being shown at resonance and at 10% detuning and with the error produced by the detuning being shown at constant quality factor and excitation in dependence on the time.

To make the test method of the invention clearer, reference is also made to FIGS. 4 and 5.

In FIG. 4 the time dependencies of the demodulated transducer currents I are represented for an original quality factor of 20, and also with a reduction of the quality factor to the half value of 10, as well as the error Δ resulting therefrom.

FIG. 5 shows in analog manner the time dependencies of the demodulated transducer currents I at resonance R on the one hand, and on detuning V of 10% on the other hand, and also the error curve Δ which results therefrom.

It is clear from FIGS. 4 and 5 that the error increases with the distance from the start of the pulse timewise, both with a quality factor change of the ultrasonic converters 10, 20 and also with a detuning of 10% relative to resonance. Through a correspondingly long excitation of the transducer and exploitation of the current difference at the end of the excitation the test method can thus be made very sensitive.

The test cycles are expediently carried out automatically in specific time intervals, for which purpose the change-over switches 13, 23 are automatically switched over into the test position by the control/evaluation unit 30 at the corresponding time points. For this purpose the evaluation unit is connected to the switches 13, 23 via control lines 25, 35.

The function of the described method and of the described circuit arrangement is as follows:

In the control/evaluation unit 30, the actual envelope curves obtained from the received signals of the ultrasonic converters 10 and 20 are stored. The point of inflection WP of the envelope curve prior to reaching the maximum is then sought and the time spacing of this point of inflection WP from an arbitrarily selected zero time point is determined. Thereafter the control/evaluation unit 30 calculates that point FP on the envelope curve where the amplitude has a predetermined fraction of the amplitude at the point of inflection WP, for example 34% thereof. The time spacing of the so-called fraction point FP from the arbitrarily selected zero time point is determined.

If the amplitude of the envelope curve at the point of inflection WP is designated with "a" and if the amplitude at the fraction point FP is designated with "b", then a reference time point $t_0$ which comes very close to the true zero point of the envelope curve can be found via the times $t_w$ and $t_f$ determined at a and b in accordance with the above formula (2), with k representing the reciprocal of the predetermined fraction of the amplitude a at the point of inflection WP. Thus a/b=k. A knowledge of the absolute values of a and b is not required because, in accordance with the present invention, one is only concerned with the ratio of these amplitudes, which must, however, be preset.

With the so determined time point $t_0$, a defined transit time measurement can now be effected with the known method and thus the flow speed measurement can be effected.

The method in accordance with the present invention for the precise and reliable transit time determination of ultrasonic signals, the shape of which changes as a result of fluctuating quality or resonant frequency of the converter, thus lies in recording the time at two points of the envelope curve. Of these points, one is preferably the point of inflection and the other is a point whose amplitude is smaller than the amplitude at the point of inflection by a predetermined factor, for example 0.34. Furthermore, in order to recognize impermissible changes at the converters, the plot of the converter current flowing at the end of the excitation period is compared with the stored plot as measured in the desired state and evaluated.

What is claimed is:

1. A method of determining a time point of the start of a high frequency oscillation packet, triggered as a result of corresponding external excitation, the method comprising:
   specifying a zero point in time; and
   determining relative times at at least two points of an envelope curve of the oscillation packet, the relative times being related to the zero point in time, one of the at least two points of the envelope curve being an envelope curve point characteristic of the envelope curve and one of the at least two points having an amplitude equal to a predetermined fraction of the amplitude of the envelope curve point.

2. A method in accordance with claim 1 wherein the envelope curve point is the first point of inflection of the envelope curve.

3. A method in accordance with claim 1 wherein the fraction of the amplitude of the envelope curve point, at which one of the relative times is determined, is in the range of 0.2 to 0.8.

4. A method in accordance with claim 3 wherein the fraction of the amplitude of the envelope curve point is in the range of 0.3 to 0.5.

5. A method in accordance with claim 4 wherein the fraction of the amplitude of the envelope curve point is 0.34.

6. A method in accordance with claim 1 wherein the time point of the start of a high frequency oscillation packet is specified in accordance with the following formula:

$$t_0 = (k^* t_f - t_w)/(k-1),$$

wherein:

$t_w$ signifies the time measured from an arbitrarily selected zero time point until a point of inflection is reached;

$t_f$ signifies the time measured from the same arbitrarily selected time point at which the predetermined fraction of the envelope curve value at the point of inflection is measured; and k signifies the reciprocal of the predetermined fraction of the envelope curve value at the point of inflection, i.e. the reciprocal ratio of a first envelope curve value at the point of inflection relative to a second envelope curve value, the second envelope curve value corresponding to the predetermined fraction of the first envelope curve value at the point of inflection.

7. A method in accordance with claim 1 wherein the method is used during the reception of pulse packets at ultrasonic converters in order to determine the zero time point of the pack of oscillation arriving at the receiving converter.

8. A method in accordance with claim 7 wherein the method is used during alternate transmission and reception of pulse packets by two ultrasonic converters arranged at a flowing medium that respectively alternately transmit and receive pulse packets at an angle to direction of flow, the angle being approximately 45°, with flow speed of the medium being determined from transit time differences of the pulse packets in direction of flow for transmit and direction of flow for receive.

9. A circuit arrangement for specifying a time point of the start of a high frequency oscillation packet, triggered as a result of a corresponding external excitation, the circuit arrangement comprising a control evaluation unit wherein times of at least two points of an envelope curve of the oscillatory packet are determined in relation to a zero time point, one of the at least two points being an envelope curve point characteristic of the envelope curve and one of the at least two points having an amplitude equal to a predetermined fraction of the amplitude at the envelope curve point.

10. A circuit arrangement in accordance with claim 9 wherein the control/evaluation unit determines a first point of inflection of the envelope curve as the envelope curve point.

11. A circuit arrangement in accordance with claim 9 wherein the control/evaluation unit specifies a predetermined fraction of the amplitude of the envelope curve point to be in the range of 0.2 to 0.8.

12. A circuit arrangement in accordance with claim 11 wherein the predetermined fraction of the amplitude of the envelope curve point is in the range of 0.3 to 0.5.

13. A circuit arrangement in accordance with claim 12 wherein the predetermined fraction of the amplitude of the envelope curve point is 0.34.

14. A circuit arrangement in accordance with claim 9 wherein the control/evaluation unit determines the time point of the start of the high frequency oscillation packet in accordance with the following formula:

$$t_0 = (k^* t_f - t_w)/(i\ k-1),$$

wherein:

$t_w$ signifies the time measured from an arbitrarily selected zero time point until a point of inflection is reached;

$t_f$ signifies the time measured from the same arbitrarily selected time point at which the predetermined fraction of the envelope curve value at the point of inflection is measured; and k signifies the reciprocal of the predetermined fraction of the envelope curve value at the point of inflection, i.e. the reciprocal ratio of a first envelope curve value at the point of inflection relative to a second envelope curve value, the second envelope curve value corresponding to the predetermined fraction of the first envelope curve value at the point of inflection.

15. A circuit arrangement in accordance with claim 9 wherein the circuit arrangement is used for the measurement of the flow speeds of gases by means of a transit time difference method.

16. A circuit arrangement in accordance with claim 9 wherein the circuit arrangement further comprises at least one ultrasonic converter that is connected to a transmitter via a change-over switch with a receiver, the control/evaluation unit being connected to both the transmitter and the receiver, and a resistor is arranged between the converter and earth and can be selectively connected via the change-over switch to the receiver in order to store digitized scanning values of an output current of the converter, the output current being in a state of being compared to the memory of the evaluation unit and to compare the digitized scanning values with a desired value stored in the evaluation unit.

* * * * *